(12) United States Patent
Lee et al.

(10) Patent No.: US 6,712,833 B1
(45) Date of Patent: Mar. 30, 2004

(54) METHOD OF MAKING A CATHETER BALLOON

(75) Inventors: Jeong S. Lee, Diamond Bar, CA (US); Jose A. Romero, Perris, CA (US); Roseminda J. White, Wildomar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 42 days.

(21) Appl. No.: 09/935,449

(22) Filed: Aug. 22, 2001

(51) Int. Cl.[7] .............................................. A61M 29/00
(52) U.S. Cl. ....................................... 606/194; 606/191
(58) Field of Search ................................. 606/191, 192, 606/194, 195, 200, 108; 604/96.01

(56) References Cited

U.S. PATENT DOCUMENTS

| | | | | |
|---|---|---|---|---|
| 4,976,690 A | * | 12/1990 | Solar et al. ................. | 606/194 |
| 5,002,559 A | * | 3/1991 | Tower ......................... | 606/194 |
| 5,045,061 A | * | 9/1991 | Seifert et al. ............... | 606/194 |
| 5,087,394 A | | 2/1992 | Keith ........................... | 204/22 |
| 5,295,962 A | * | 3/1994 | Crocker et al. ............. | 606/194 |
| 5,334,146 A | * | 8/1994 | Ozasa ......................... | 606/194 |
| 5,368,566 A | * | 11/1994 | Crocker ...................... | 604/101.02 |
| 5,470,313 A | * | 11/1995 | Crocker et al. ............ | 604/103.07 |
| 5,549,553 A | * | 8/1996 | Ressemann et al. ... | 604/103.08 |
| 5,587,125 A | * | 12/1996 | Roychowdhury ........... | 606/194 |
| 5,645,789 A | * | 7/1997 | Roucher, Jr. ................ | 606/194 |
| 5,714,110 A | | 2/1998 | Wang et al. ................ | 264/529 |
| 5,792,415 A | * | 8/1998 | Hijlkema ..................... | 264/530 |
| 5,807,520 A | | 9/1998 | Wang et al. ................ | 264/520 |
| 6,004,289 A | * | 12/1999 | Saab .......................... | 606/194 |
| 6,465,067 B1 | * | 10/2002 | Wang et al. ................ | 606/192 |

\* cited by examiner

*Primary Examiner*—Michael J. Milano
*Assistant Examiner*—Jessica R Baxter
(74) *Attorney, Agent, or Firm*—Fulwider Patton Lee & Utecht, LLP

(57) ABSTRACT

A method of forming a catheter component, such as a balloon, in which the component has a thinned skirt section formed by expanding tubing to a radially enlarged outer diameter and then decreasing the inner diameter and the outer diameter of the radially enlarged skirt section before or during bonding of the skirt section to the catheter shaft. The method generally includes blow molding tubing in a balloon mold having a skirt portion with an inner diameter which is larger than an outer diameter of the thinned skirt section of the balloon, so that the balloon mold produces a balloon having a radially enlarged skirt section with a larger outer diameter than is desired for the finished balloon. By then decreasing the diameter of the radially enlarged skirt section, the resulting skirt section is thinned, to provide a balloon catheter having improved flexibility and low profile.

12 Claims, 2 Drawing Sheets

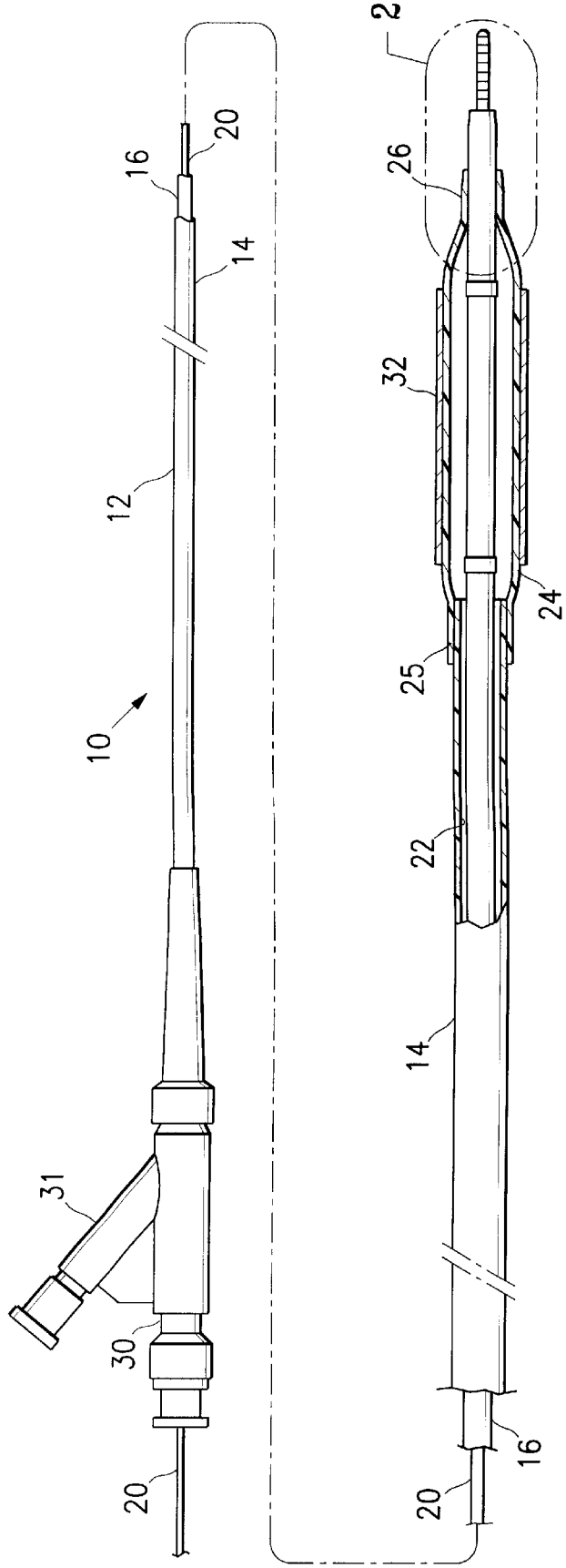
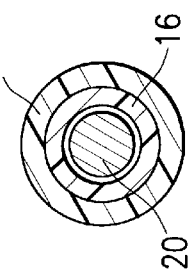
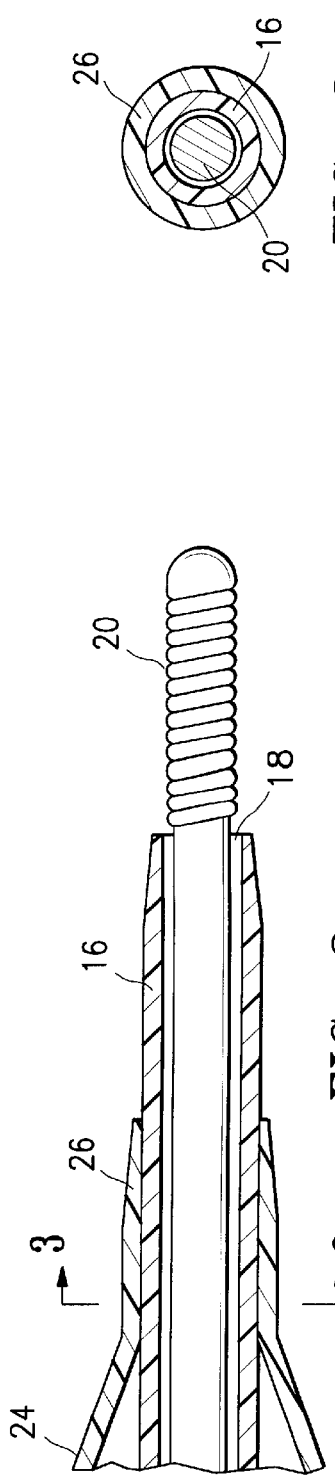

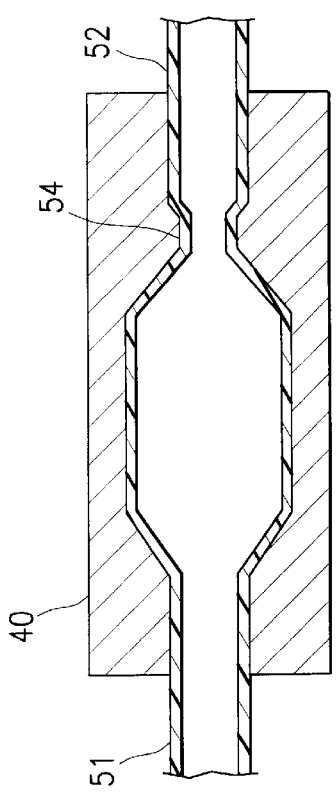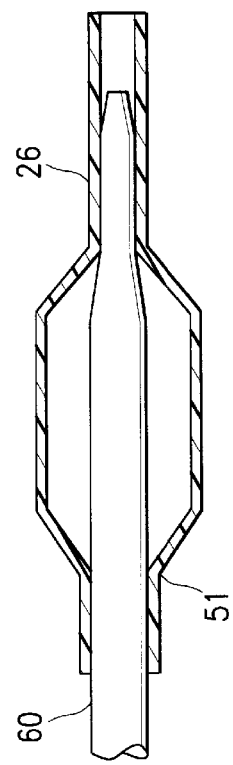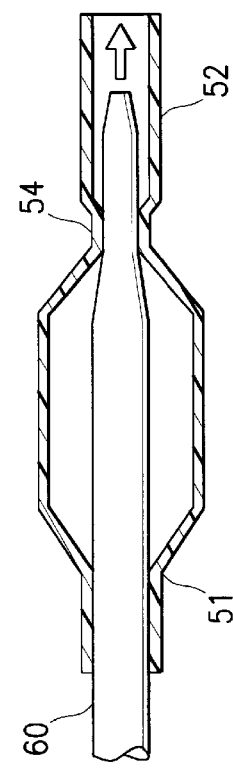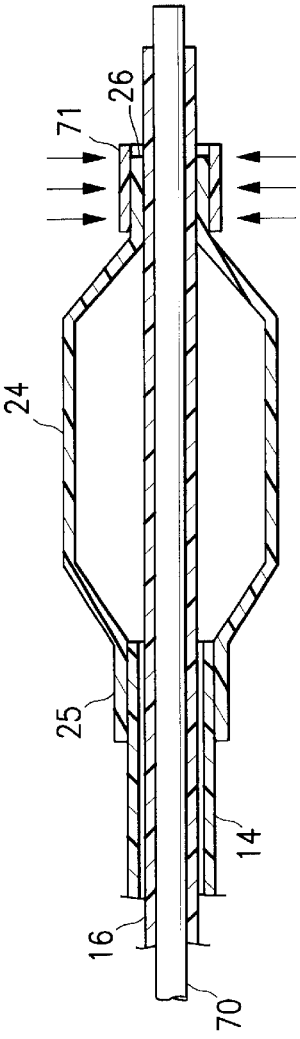

METHOD OF MAKING A CATHETER BALLOON

BACKGROUND OF THE INVENTION

This invention generally relates to medical devices, and particularly to balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter, and the stent left in place within the artery at the site of the dilated lesion.

In the design of balloon catheters, catheter characteristics such as flexibility, pushability, and profile must be tailored to provide optimal performance for a particular application. Angioplasty balloon catheters are preferably flexible yet pushable and with a low profile for improved ability to track the tortuous anatomy and cross lesions with the balloon in the uninflated state. A distal section with a low profile, i.e., a small leading outer diameter, is necessary to guide the catheter to the location of the lesion with as little damage to the patient's body lumen as possible. During balloon manufacture, a polymeric tube is formed into a finished balloon having a desired outer diameter and length. The skirt sections of the balloon are then bonded to the shaft. The manufacturing process may create a step increase in outer diameter from the catheter distal tip to the balloon, or an increase in catheter stiffness at the bond between the balloon and the shaft, which consequently may create a higher profile and cause damage and difficulty moving the catheter through the body lumen. When extruded tubing with a constant inner and outer diameter is blow molded to form a balloon, the balloon typically has a thin working length and a disadvantageously thick skirt section. This is due to the fact that the balloon working length has a blow-up-ratio (BUR) (i.e., balloon outer diameter divided by the tubing inner diameter) which is higher than the BUR of the skirt sections.

What has been needed is an improved method of forming a catheter balloon having a thin walled skirt section.

SUMMARY OF THE INVENTION

This invention is directed to a method of forming a catheter component, such as a balloon for a catheter, in which the component has a thinned skirt section formed by expanding tubing to a radially enlarged outer diameter and then decreasing the inner diameter and the outer diameter of the radially enlarged skirt section before or during bonding of the skirt section to a section of the catheter shaft. While discussed below primarily in terms of a balloon, it should be understood that other catheter components such as soft distal tips and shaft sections can be formed with a thinned end section using the method of the invention. The method generally includes blow molding tubing in a balloon mold to form the balloon, the balloon mold having a skirt portion for forming the radially enlarged skirt section, and having an interior surface which corresponds to the desired form of the working length and tapered sections of the balloon. The skirt portion of the balloon mold has an inner diameter which is larger than an outer diameter of the thinned skirt section of the balloon, so that the balloon mold produces a balloon having a radially enlarged skirt section with a larger outer diameter than is desired for the finished balloon. Thus, by first expanding the tubing in the balloon mold, and then decreasing the inner and outer diameter of the radially enlarged skirt section, the resulting skirt section of the balloon has a thinned skirt section which provides a balloon catheter having improved flexibility and low profile.

Balloons of the invention, as with conventional catheter balloons such as angioplasty or stent delivery balloons, typically have a working length configured to expand to perform a procedure such as dilatation of a lesion or implantation of a stent. The balloon has a proximal tapered section at a proximal end of the working length, a proximal skirt section at a proximal end of the proximal tapered section for securing the balloon to a catheter shaft, a distal tapered section at a distal end of the working length, and a distal skirt section at a distal end of the distal tapered section for securing the balloon to a catheter shaft. The expanded outer diameter of the radially enlarged skirt section is larger than the outer diameter of the end of the tapered section adjacent thereto. In a conventional balloon mold, the mold interior portion which forms a skirt section of the balloon has an inner diameter which is the same as or smaller than the inner diameter of the adjacent end of the adjacent tapered section. As a result of expanding the skirt section to a larger diameter than in a conventional mold, the skirt section formed according to the method of the invention has a thinner wall thickness than would otherwise be produced by a balloon blow molded in a conventional balloon mold. In one embodiment, a balloon of the invention having a 3.0 mm nominal inflated outer diameter has a thinned distal skirt section wall thickness of less than about 0.036 mm to about 0.04 mm, and a balloon having a 5.0 mm nominal inflated outer diameter has a thinned distal skirt section wall thickness of less than about 0.11 mm to about 0.13 mm, and, specifically, a thinned wall thickness of about 0.08 mm to about 0.09 mm.

In a presently preferred embodiment, the inner and outer diameter of the radially enlarged skirt section is decreased by necking the radially enlarged skirt section before bonding to the catheter shaft. The radially enlarged skirt section is preferably necked by applying heat and axial tension to the radially enlarged skirt section to thereby decrease the inner and outer diameter and further decrease the wall thickness of the skirt section. The necked skirt section is then fusion or adhesively bonded to the catheter shaft. In the embodiment in which the necked skirt is fusion bonded to the shaft, the wall thickness of the skirt section is further decreased by causing the skirt section polymeric material to flow during the fusion bonding. In a presently preferred embodiment, the balloon tubing is expanded in the balloon mold so that the radially enlarged skirt section has an inner and outer diameter greater than an inner and outer diameter of an intermediate section located between the radially enlarged section and the tapered section adjacent thereto. The smaller inner diameter of the intermediate section is preferably configured to facilitate gripping of the balloon onto a mandrel positioned in the balloon during necking of the radially enlarged skirt section.

Catheter balloons, and particularly angioplasty and stent delivery balloons, having thin skirt sections provide higher flexibility than balloons with thick skirt sections, and therefore provide easier access to a lesion in a blood vessel. A thin skirt is especially critical at the distal skirt which comes into contact with the lesion first. The method of the invention may be used to form the proximal and/or the distal skirt section of the balloon with a thinned wall thickness. However, in a presently preferred embodiment, at least the distal skirt section is formed with a thinned wall thickness according to the method of the invention, in order to provide improved flexibility and low profile at the distal end of the catheter for improved ability to cross a lesion.

The balloons of the invention may be used on a variety of catheter types, including dilatation catheters, such as angioplasty catheters, and stent delivery catheters, and the like. A presently preferred embodiment of the invention is a peripheral balloon catheter. In one embodiment, the peripheral balloon catheter has a balloon with an inflated working outer diameter of at least 4 mm, and preferably about 5 mm to about 10 mm. Peripheral balloon catheters typically have balloons with a larger outer diameter than coronary balloon catheters, for use in large peripheral blood vessels. Such large balloons generally have skirt sections with a large wall thickness unless thinned before or after blow molding of the balloon. Necking procedures which thin the skirt section by axially stretching the balloon tubing, typically before blow molding of the balloon, produce disadvantageous orientation in the polymer molecules. As the degree of orientation increases, it becomes more difficult to expand the pre-necked portion of the balloon tubing. Therefore, the amount of skirt thinning possible from pre-necking the balloon tubing is limited. The method of the invention thins the skirt section in part by first expanding the skirt section to the radially enlarged diameter. Consequently, unlike pre-necking, the method of the invention results in thinned balloon skirt sections without disadvantageously axially orienting the polymer molecules, and thus provides for optimum skirt thinning.

Although discussed primarily in terms forming a balloon for a balloon catheter, the invention should be understood to include other components for medical devices such as a catheter distal tip or shaft, in which thinning a section of the component is desired.

The method of the invention provides for improved manufacture of a catheter balloon having a thinned skirt section, due to the expansion of the skirt section to a radially enlarged outer diameter and decreasing the inner and outer diameter of the radially enlarged skirt section before or during bonding the skirt section to the catheter shaft. The balloon thus formed provides a catheter with improved flexibility and low profile, for improved trackability and crossability. These and other advantages of the invention will become more apparent from the following detailed description when taken in conjunction with the accompanying exemplary drawings.

BRIEF DESCRIPTION OF THE DRAWINGS

FIG. 1 is an elevational view, partially in section, of a balloon catheter for delivering a stent, having a balloon formed according to a method that embodies features of the invention.

FIG. 2 is a longitudinal, enlarged, cross sectional view of the distal end of the catheter shown in FIG. 1, taken within circle 2.

FIG. 3 is a transverse cross-section of the catheter shown in FIG. 2, taken at line 3—3.

FIG. 4 is a longitudinal cross sectional view a balloon mold having balloon tubing therein prior to being radially expanded in the balloon mold, according to a method that embodies features of the invention.

FIG. 5 illustrates the balloon mold and balloon tubing therein shown in FIG. 4, after the balloon tubing is radially expanded in the balloon mold, to form a balloon with a radially enlarged skirt section according to a method which embodies features of the invention.

FIG. 6 is a longitudinal cross sectional view of the expanded balloon tubing shown in FIG. 5, with a mandrel in the balloon in preparation for necking of the radially enlarged skirt section outside of the balloon mold.

FIG. 7 is a longitudinal cross sectional view of the expanded balloon tubing shown in FIG. 6, after the radially enlarged skirt section is necked.

FIG. 8 is a longitudinal cross sectional view of the balloon shown in FIG. 7, during bonding of the distal skirt section to a catheter shaft.

DETAILED DESCRIPTION OF THE INVENTION

FIG. 1 illustrates an over-the-wire type stent delivery balloon catheter 10 embodying features of the invention. Catheter 10 generally comprises elongated catheter shaft 12 having an outer tubular member 14 and an inner tubular member 16. Inner tubular member 14 defines a guidewire lumen 18 (FIG. 2) configured to slidingly receive a guidewire 20. The coaxial relationship between outer tubular member 14 and inner tubular member 16 defines annular inflation lumen 22. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, an expandable stent 32 is mounted on uninflated balloon 24. The distal end of catheter may be advanced to a desired region of a patient's body lumen in a conventional manner and balloon 24 may be inflated to expand stent 32, seating it in the lumen. FIGS. 2 and 3 illustrate a longitudinal and a transverse cross section view, respectively, of the distal end of the catheter shown in FIG. 1, taken within circle 2 of FIG. 1 and along line 3—3 of FIG. 2, respectively.

At least one of the proximal skirt section 25 and the distal skirt section 26 has a wall thickness thinned according to a method of the invention. In a presently preferred embodiment, at least the distal skirt section 26 has a wall thickness thinned according to a method of the invention. FIG. 4 illustrates a longitudinal cross sectional view of a balloon mold 40 for forming a catheter balloon having a thinned distal skirt section, according to a method which embodies features of the invention. Mold 40 has an interior chamber 41 with a first portion 42 having an interior surface and comprising portions 42a, 42b, and 42c. The interior surface of portion 42a corresponds to the desired form of the working length, and the interior surface of portions 42b and 42c correspond to the desired form of the proximal and distal tapered sections of the balloon, respectively. Mold 40 has a second portion 44 for forming at least a section of the distal skirt section 26 of the balloon. The second portion 44 has an inner diameter which is larger than the outer diameter of the distal skirt section 26 of the balloon. Additionally, the inner diameter of the second portion 44 of the mold is greater than the inner diameter of the distal end of the tapered portion 42c which forms the distal end of the distal tapered section of the balloon. Mold has a third portion 46 having an interior surface which corresponds to the desired form of the proximal skirt section 25 of the balloon.

In the embodiment illustrated in FIG. 4, the mold includes an intermediate portion 48 between the tapered portion 42c and the second portion 44, having an inner diameter which is smaller than the inner diameter of the second portion 44. A tapered section extends between the intermediate portion 48 and the second portion 44. In the embodiment illustrated in FIG. 4, the intermediate portion 48 has an interior surface substantially parallel to the interior surface of the second portion 44 of the mold. The terminology substantially parallel should be understood to mean that the surfaces of the portions extend in the same direction with axially aligned surfaces within the normal tolerances of balloon mold formation. Thus, the surfaces of the intermediate and second portions 48, 44 do not deliberately extend at an angle with respect to one another.

A length of balloon tubing 50, typically formed by extruding a polymeric material into a tubular shape, is illustrated in FIG. 4 in mold 40, before being radially expanded in the mold. The tubing 50 is radially expanded at elevated temperature and pressure, and optionally under axial tension, in the mold 40, to form expanded tubing 51. The tubing expands into contact with the interior surface of the mold 40 to form the balloon working length and tapered sections, as best illustrated in FIG. 5 showing the expanded tubing 51 in the mold 40. A distal section of the tubing 50 expands into contact with the interior surface of the second portion 44 to form a radially enlarged distal skirt section 52. In one embodiment, the wall thickness of the radially enlarged distal skirt section 52 is sufficient to allow for a further reduction of the wall thickness of the skirt section as for example during bonding thereof to a catheter shaft. The inner diameter of the intermediate portion 48 of the mold is typically sized so that the tubing 50 radially expands during blow molding into contact with the interior surface of intermediate portion 48 of the mold to form intermediate section 54 of the expanded tubing 51. However, in alternative embodiments, there may be little or no radial expansion of the tubing 50 at the intermediate portion 48 of the mold, where the inner diameter of the intermediate portion 48 is substantially similar to the unexpanded outer diameter of the tubing 50 located therein.

After the tubing 50 is expanded in the mold to form expanded tubing 51, the inner and outer diameter of the radially enlarged distal skirt section 52 is decreased. In one embodiment, the inner and outer diameter of the radially enlarged distal skirt section 52 is decreased at least in part by necking the section 52 prior to bonding to the catheter shaft 12. In a presently preferred embodiment, the section 52 is necked outside of the balloon mold 40, in order to avoid affecting other sections of the balloon such as the tapered sections during the necking process. FIG. 6 illustrates the tubing 50 after being expanded in mold 40 and removed therefrom, prior to necking of the radially enlarged distal skirt section 52. A mandrel 60 is placed in the interior of the expanded tubing and the radially enlarged distal skirt section 52 is necked by applying heat and axial tension. As illustrated in FIG. 6, the intermediate section 54 of the expanded tubing 51 has an inner diameter about equal to the outer diameter of the mandrel 60, and thus grips the mandrel to facilitate the necking process. Preferably, the radially enlarged distal skirt section 52 is the only section of the expanded tubing 51 which is heated during necking, as for example, by providing a heat shielding cover over the intermediate section 54 of the expanded tubing and sections proximal thereto, and using a heat nozzle to direct the heat applied to the expanded tubing. Thus, the intermediate section 54 is not heated during necking, which, as a result, allows the radially enlarged distal skirt section 52 to be necked without affecting the distal tapered section. FIG. 7 illustrates the expanded tubing shown in FIG. 6, after necking of the radially enlarged distal skirt section 52 to decrease the inner and outer diameter thereof, and form the thinned distal skirt section 26 of the balloon. After necking, the thinned skirt section of the balloon may be trimmed to a shorter length before bonding to the catheter shaft. For ease of illustration, the decrease in wall thickness produced when the tubing is radially expanded and necked is not illustrated in the figures.

FIG. 8 illustrates the balloon 24 during bonding of the thinned distal skirt section 26 of the balloon 24 to the inner tubular member 16. The proximal skirt section 25 of the balloon 24 is around the outer tubular member 14, and a mandrel 70 is within the lumen of the inner tubular member 16 for support during the bonding. In the embodiment illustrated in FIG. 8, the thinned distal skirt section 26 is being fusion bonded to the shaft by applying heat to the thinned distal skirt section 26. A heat shrink tube 71 is around an outer surface of the thinned distal skirt section 26 applies a radially compressive force to the thinned distal skirt section 16 during the fusion bonding. As a result of fusion bonding, the polymeric material of the thinned distal skirt section 26 typically flows during bonding to further reduce the outer diameter and wall thickness of the thinned skirt section 26.

Either or both of the proximal and distal skirt sections 25, 26 may be further processed after formation, as is conventionally known, as for example by further removing polymeric material from the skirt sections, axially or radially expanding or contracting the skirt sections, annealing or otherwise heat treating the skirt sections, and the like. Additionally, the balloon tubing may be axially stretched in the mold during the blow molding process, as is conventionally known for balloon blow molding.

Extruded tubing 50 typically has an outer diameter of about 1.2 to about 3.1 mm, and an inner diameter of about 0.6 to about 1.8 mm. Radially enlarged distal skirt section 52 of the expanded tubing 51 typically has an outer diameter of about 0.8 to about 2.5 mm, and an inner diameter of about 0.6 to about 1.7 mm. The balloon thinned distal skirt section 26, after necking, typically has an outer diameter of about 0.8 to about 1.2 mm, and an inner diameter of about 0.6 to about 0.8 mm. Thus, the thinned distal skirt section 26 typically has a wall thickness which is about 10% to about 50% less than the wall thickness which would otherwise be produced in a convention balloon mold having a skirt portion which isn't radially enlarged according to the invention. After bonding the balloon thinned distal skirt section 26 to the catheter shaft, the thinned distal skirt section 26 typically has an outer diameter of about 0.7 to about 1.15 mm, and an inner diameter equal to the inner diameter before bonding. The balloon is blow molded using processing conditions which produce the balloon having the thinned skirt section with a desired wall thickness. For example, in one embodiment, a PEBAX 72D balloon having a 3.0 mm nominal outer diameter is blow molded from extruded and necked tubing, by heating at about 410° F. to about 430° F., preferably about 420° F., and pressurizing at a pressure of about 460 psi. Axial tension of about 50 grams to about 650 grams is applied at various locations along the length of the tubing during blowing, and the tubing is heated by traversing a heating nozzle at a speed of about 2.3 to about 4.0 mm/second along the length of the mold with the tubing therein. The outer diameter and inner diameter of the resulting radially enlarged distal skirt section after blow molding but before being decreased according to the invention, is about 0.85 mm and about 0.65 mm, respectively.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and wall thickness of 0.004 to 0.008 inch (0.01 to 0.02 cm). The overall length of the catheter 10 may range from about 100 to about 150 cm, and is typically about 135 cm. Preferably, balloon 24 may have a length about 0.5 cm to about 6 cm, and an inflated working diameter of about 3 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is over-the-wire stent delivery catheter, balloons of this invention may also be used with other types of intravascular catheters, such as and rapid exchange dilatation catheters. Rapid exchange catheters generally comprise a distal guidewire port in a distal end of the catheter and a proximal guidewire port distal of the proximal end of the shaft, and typically spaced a substantial distance from the proximal end of the catheter, and a short guidewire lumen extending between the proximal and distal guidewire ports in a distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of making a catheter balloon having a thinned skirt section for securing the balloon to a catheter, comprising:
    a) blow molding tubing to form expanded tubing with a radially enlarged skirt section by expanding the tubing in a balloon mold having a skirt portion for forming the radially enlarged skirt section, the skirt portion of the balloon mold having an inner diameter which is larger than an outer diameter of the thinned skirt section of the balloon, and wherein the tubing is expanded in the balloon mold such that the inner diameter of the radially enlarged skirt section is greater than an inner diameter of an intermediate section of the expanded tubing between the radially enlarged skirt section and a tapered section adjacent thereto; and
    b) decreasing an inner diameter and the outer diameter of the radially enlarged skirt section, to form the thinned skirt section of the balloon.

2. The method of claim 1 wherein (b) comprises necking the radially enlarged skirt section by applying heat and axial tension to the radially enlarged skirt section to thereby decrease the outer diameter and wall thickness of the radially enlarged skirt section.

3. The method of claim 2 including removing the expanded tubing from the balloon mold before necking of the radially enlarged skirt section.

4. The method of claim 2 wherein a mandrel is inserted into a lumen of the expanded tubing before necking the radially enlarged skirt section, and the radially enlarged skirt section is necked down onto the mandrel.

5. The method of claim 1 wherein (b) comprises applying heat and a radially compressive force to the radially enlarged skirt section.

6. The method of claim 1 wherein the balloon has a proximal skirt section and a distal skirt section, and the thinned skirt section is the distal skirt section.

7. The method of claim 1 wherein the balloon has a proximal skirt section and a distal skirt section, and the thinned skirt section is the proximal skirt section.

8. The method of claim 1 wherein the balloon mold has two skirt portions for forming a proximal radially enlarged skirt section and a distal radially enlarged skirt section, and forming the balloon comprises blow molding the tubing to form the expanded tubing with the proximal radially enlarged skirt section and the distal radially enlarged skirt section, and decreasing the proximal radially enlarged skirt section inner and outer diameter, and decreasing the proximal radially enlarged skirt section inner and outer diameter, to form the balloon having a thinned proximal skirt section and a thinned distal skirt section.

9. A method of making a catheter balloon having a working length, proximal and distal tapered sections at either end of the working length, and proximal and distal skirt sections for securing the balloon to a catheter shaft, at least one of the proximal and distal skirt sections being a thinned skirt section, comprising:

a) placing tubing in a balloon mold having a first portion with an interior surface which corresponds to the desired form of the working length and tapered sections of the balloon, and having a skirt portion for forming the thinned skirt section of the balloon, the skirt portion having an inner diameter which is larger than an outer diameter of the thinned skirt section of the balloon, and having an intermediate portion between the skirt portion and the first portion with an inner diameter smaller than the inner diameter of the skirt portion;

b) expanding the tubing in the balloon mold to form the balloon having a radially enlarged skirt section, and an intermediate section between the radially enlarged skirt section and the tapered section adjacent thereto with a smaller outer diameter than the radially enlarged skirt section; and c) decreasing an inner diameter and the outer diameter of the radially enlarged skirt section, to form thinned skirt section.

10. The method of claim 9 wherein (c) comprises necking the radially enlarged skirt section by applying heat and axial tension to the radially enlarged skirt section to thereby decrease the inner and outer diameter and wall thickness of the radially enlarged skirt section.

11. A method of making a catheter balloon having a working length, proximal and distal tapered sections at either end of the working length, and proximal skirt section and a thinned distal skirt section for securing the balloon to catheter shaft, comprising:

a) placing tubing in a balloon mold;

b) expanding a first section of the tubing in the balloon mold to form the working length and the proximal tapered section and the distal tapered section of the balloon; and c) expanding a second section of the tubing to form a radially enlarged distal skirt section having an expanded outer diameter greater than an outer diameter of a distal end of the distal tapered section adjacent thereto, and decreasing the expanded outer diameter of the radially enlarged distal skirt section to form the thinned distal skirt section of the balloon, to form the balloon wherein a third section of tubing forms an intermediate section located between the distal tapered section and the radially enlarged distal skirt section, the third section having a smaller inner and outer diameter than the radially enlarged distal skirt section.

12. The method of claim 11 wherein decreasing the expanded outer diameter of the second section comprises necking the radially enlarged distal skirt section by applying heat and axial tension to the radially enlarged distal skirt section to thereby decrease the outer diameter and wall thickness of the radially enlarged distal skirt section.

* * * * *